US00PP36207P2

(12) United States Plant Patent
Rupp

(10) Patent No.: US PP36,207 P2
(45) Date of Patent: Oct. 15, 2024

(54) ***GAURA* PLANT NAMED 'KLEGL22507'**

(50) Latin Name: *Gaura lindheimerii*
Varietal Denomination: KLEGL22507

(71) Applicant: KLEMM + SOHN GMBH & CO. KG, Stuttgart (DE)

(72) Inventor: Judith Rupp, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/223,692

(22) Filed: Jul. 19, 2023

(51) Int. Cl.
*A01H 5/02* (2018.01)
*A01H 6/00* (2018.01)

(52) U.S. Cl.
USPC ..... Plt./432

(58) Field of Classification Search
USPC ..... Plt./432
See application file for complete search history.

(56) References Cited

PUBLICATIONS https://devilmountainnursery.com/gaura-lindheimeri-belleza-dark-pink/ Retrieved from the Internet on May 30, 2024.*

* cited by examiner

*Primary Examiner* — Susan McCormick Ewoldt
(74) *Attorney, Agent, or Firm* — Weatherly IP Solutions, LLC; James M. Weatherly

(57) ABSTRACT

A new *Gaura* plant particularly distinguished by having a dark pink petal color and an earliness of 10 weeks from potting, is disclosed.

1 Drawing Sheet

Genus and species: *Gaura lindheimerii.*
Variety denomination: 'KLEGL22507'.

BACKGROUND OF THE NEW PLANT

The present invention comprises a new and distinct variety of Gaura, botanically known as *Gaura lindheimerii*, and hereinafter referred to by the variety name 'KLEGL22507'. 'KLEGL22507' originated from an open pollination between the female Gaura variety 'KLEAU04263' (unpatented) and an unknown male Gaura variety.

From May 2008through August of 2008open cross pollination took place between the female Gaura variety 'KLEAU04263' and an unknown male Gaura variety. Seed was collected and cleaned in the winter of 2008. In January 2009, seed were sown and plants were grown for evaluation in Stuttgart, Germany in a greenhouse under glass. A plant line was selected in May 2009and subsequently named 'KLEGL22507'. In May 2009, 'KLEGL22507' was first vegetatively propagated in Stuttgart, Germany by asexual cuttings. 'KLEGL22507' was found to reproduce true to type in successive generations of asexual propagation via cuttings.

SUMMARY

The following are the most outstanding and distinguishing characteristics of this new variety when grown under normal horticultural practices in Stuttgart, Germany.

1. A dark pink petal color; and
2. An earliness of 10 weeks from potting.

DESCRIPTION OF THE PHOTOGRAPH

This new Gaura plant is illustrated by the accompanying photograph. The photograph is of a 12-week-old plant grown in an indoor environment in Stuttgart, Germany in May 2022. The colors shown are as true as can be reasonably obtained by conventional photographic procedures.

DESCRIPTION OF THE NEW VARIETY

The following detailed descriptions set forth the distinctive characteristics of 'KLEGL22507'. The data which define these characteristics were collected from asexual reproductions carried out in Stuttgart, Germany. Data was collected on plants 11-weeks-old from potting grown in a foil house where no plant regulators were used in Stuttgart, Germany in May 2023. Color references are to The R.H.S. Colour Chart of The Royal Horticultural Society of London (R.H.S.), (2005).

Classification:
- *Family*.—Onagraceae.
- *Botanical*.—*Gaura lindheimerii.*
- *Common*.—Gaura.
- *Designation*.—'KLEGL22507'.

Parentage:
- *Female parent*.—'KLEAU04263'(unpatented).
- *Male parent*.—Unknown.

Propagation:
- *Type*.—Cuttings.
- *Time to initiate roots*.—Approximately 16 days.
- *Time to develop roots*.—18-21 days
- *Time to produce a flowering plant from a rooted cutting*.—10 weeks in Stuttgart, Germany spring.
- *Time to produce a rooted young plant, summer and winter*.—Approximately 18 days.

Plant description:
- *Habit*.—Upright.
- *Plant type*.—Perennial.
- *Flowering season*.—April to November.

*Plant height.*—63 cm.
*Plant diameter.*—38 cm.
*Root description.*—Fine, white roots.
*Rooting habit.*—Branching root system.
*Root color.*—RHS 155B.

Lateral branch description:
*Quantity of stems per plant.*—4 to 5.
*Branching habit.*—Open, branching from base.
*Length.*—20.0 cm to 25.0 cm.
*Diameter.*—0.2 cm.
*Internode length.*—0.8 cm to 1.3 cm.
*Strength.*—Medium.
*Texture and luster.*—Smooth and hairy.
*Pubescence.*—Sparse pubescence.
*Color.*—Developing: RHS 183A. Developed: RHS 177B.

Leaf description:
*Arrangement.*—Alternate.
*Length.*—4.0 cm to 17.0 cm.
*Width.*—0.5 cm to 2.2 cm.
*Shape.*—Oblanceolate.
*Pubescence.*—Absent.
*Apex.*—Narrowly acute.
*Base.*—Attenuate.
*Margin.*—Entire to slightly dentated.
*Texture and luster.*—Upper surface: Smooth. Lower surface: Smooth.
*Venation pattern.*—Pinnate.
*Venation color.*—Upper surface: RHS 58A. Lower surface: RHS 58C.
*Color.*—Developing leaves: Upper surface: RHS 137B. Lower surface: RHS 138A. Fully expanded leaves: Upper surface: RHS 137A. Lower surface: RHS 138A.
*Petiole.*—Absent.

Flower description:
*Flower arrangement and habit.*—Spike.
*Lastingness of the flowers.*—Longevity of the individual flowers is strongly dependent on the climate.
*Fragrance.*—Absent.
*Natural flowering season.*—April to the end of October.
*Inflorescence height.*—12.5 cm to 14.5 cm.
*Inflorescence diameter.*—4.3 cm.
*Flower diameter.*—3.4 cm.
*Flower depth.*—1.0 cm.
*Flower buds.*—Length: 1.5 cm. Diameter: 0.2 cm. Shape: Linear to narrow oval. Texture and luster: Slightly pubescent. Color: RHS 59A.
*Petals.*—Arrangement: Valvate. Number: Four per flower. Length: 1.5 cm to 1.7 cm. Width: 1.0 cm. Shape: Ovate. Apex: Rounded. Base: Cuneate. Margin: Entire. Texture and luster: Upper surface: Smooth. Lower surface: Smooth. Color: When opening: Upper surface: RHS 67B. Lower surfaces: RHS 67B. Fully opened: Upper surface: RHS 67A. Lower surface: RHS 67A. Venation: Soft venation on the petals RHS 61B.
*Sepals.*—Arrangement: Valvate. Number: Four. Length: 1.3 cm. Width: 0.3 cm. Shape: Linear. Apex: Acute. Base: Rounded. Margin: Entire. Texture and luster: Upper surface: Smooth. Lower surface: Smooth. Color: Upper surface: RHS 59A. Lower surfaces: RHS 59A.
*Pedicels.*—Length: 1.0 cm. Diameter: 0.1 cm. Strength: Strong. Texture and luster: Smooth. Color: RHS 59A.
*Peduncles.*—Length: 30.0 cm to 60.0 cm. Diameter: 0.2 cm to 0.3 cm. Color: Lower part is RHS 146B; tip is RHS 59C.

Reproductive organs:
*Stamens.*—Quantity: 8 . Filament length: 1.2 cm. Filament color: RHS 61A. Anther length: 0.3 cm. Anther shape: Ovate. Anther color: RHS 187A. Pollen amount: Moderate. Pollen color: RHS 160B.
*Pistils.*—Quantity per flower: 1 . Pistil length: 2.0 cm. Stigma shape: Lobed. Stigma color: RHS 155A. Style length: 1.9 cm. Style color: RHS 61A. Ovary color: RHS 142A.

Seeds and fruits: None observed.
Pathogen & pest resistance: None observed.
Winter hardiness and drought tolerance: Not observed.

COMPARISON WITH PARENTAL LINE AND KNOWN VARIETY

'KLEGL22507' is a distinct variety of Gaura; 'KLEGL22507' is distinguished from its female parent as described in Table 1:

TABLE 1

Comparison with Parental Line

| Trait | Variety 'KLEGL22507' | Female parent KLEAU04263 |
|---|---|---|
| Earliness from potting | 10 weeks | 12 weeks |

'KLEGL22507' is most similar to the Gaura plant Belleza White '14(unpatented). Differences between the two varieties are described in Table 2:

TABLE 2

Comparison with Similar Variety

| Trait | Variety 'GL-2009-0051' | Commercial line: Belleza White '14 |
|---|---|---|
| Petal color | Dark Pink | White to pink |

I claim:

1. A new and distinct cultivar of Gaura Plant Named 'KLEGL22507' as described and illustrated herein.

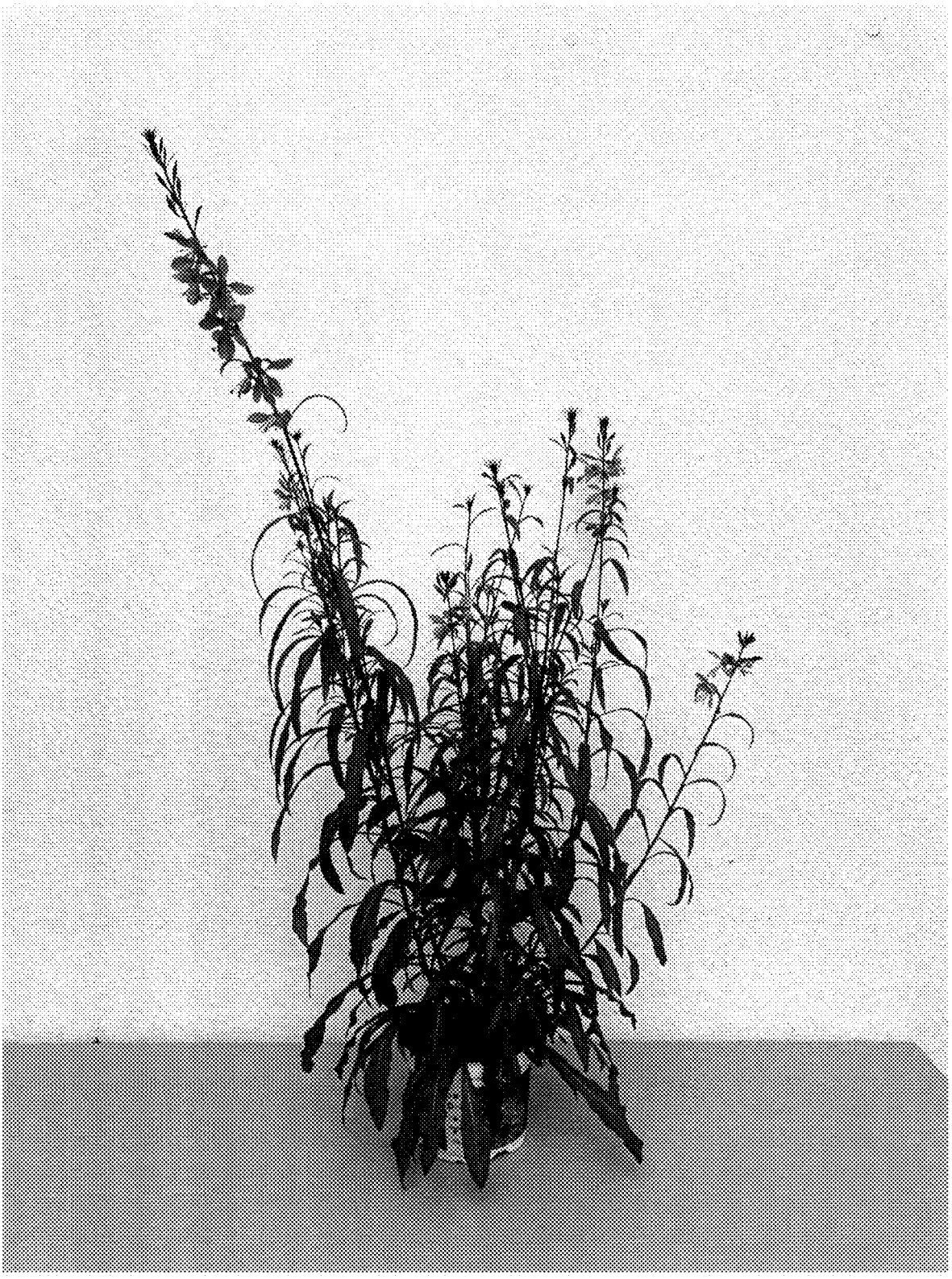

* * * * *